United States Patent
Putha et al.

(10) Patent No.: US 12,380,691 B2
(45) Date of Patent: Aug. 5, 2025

(54) SYSTEM AND METHOD FOR PROVIDING BOUNDING BOX TO FRACTURED BODY PARTS IN MUSCULOSKELETAL X-RAY

(71) Applicant: Qure.ai Technologies Private Limited, Maharashtra (IN)

(72) Inventors: Preetham Putha, Maharashtra (IN); Swetha Tanamala, Maharashtra (IN); Sahil Sahil, Maharashtra (IN); Ravi Kumar Kushawaha, Maharashtra (IN)

(73) Assignee: Qure.ai Technologies Private Limited, Mumbai (IN)

( * ) Notice: Subject to any disclaimer, the term of this patent is extended or adjusted under 35 U.S.C. 154(b) by 0 days.

(21) Appl. No.: 18/935,742

(22) Filed: Nov. 4, 2024

(65) Prior Publication Data
US 2025/0148773 A1    May 8, 2025

(30) Foreign Application Priority Data
Nov. 3, 2023 (IN) .............................. 202321075164

(51) Int. Cl.
*G06V 10/82* (2022.01)
*G06V 10/26* (2022.01)
(Continued)

(52) U.S. Cl.
CPC .............. *G06V 10/82* (2022.01); *G06V 10/26* (2022.01); *G06V 10/764* (2022.01); *G06V 40/10* (2022.01);
(Continued)

(58) Field of Classification Search
CPC ........ G06V 10/82; G06V 40/10; G06V 10/26; G06V 10/764; G06V 2201/033; G16H 15/00
See application file for complete search history.

(56) References Cited

U.S. PATENT DOCUMENTS 8,538,117 B2    9/2013   Najarian et al.
11,164,045 B2   11/2021  Paik et al.
(Continued)

FOREIGN PATENT DOCUMENTS

| CN | 108171714 B | 9/2021 |
| CN | 112598661 B | 7/2022 |
| CN | 113610809 B | 4/2024 |

OTHER PUBLICATIONS

Wu, Mingxiang, et al. "Development and evaluation of a deep learning algorithm for rib segmentation and fracture detection from multicenter chest CT images." Radiology: Artificial Intelligence 3.5 (2021): e200248. (Year: 2021).*

*Primary Examiner* — Utpal D Shah

(57) ABSTRACT

The present disclosure relates to a system (100) and method for providing bounding box to fractured body parts in musculoskeletal X-ray images. The system (100) comprises a memory unit (203) and processor (201) with a data collection module (205) gathering input X-ray data (101). Additionally, it includes a fracture detection module (206) consisting of a segmentation model (207) and an object detection model (208). The segmentation model (207) determines segmentation scores to each pixel in the X-ray image and generates a segmentation mask (404) by comparing the segmentation score of each pixel (403) with a segmentation threshold of a fracture. Simultaneously, the object detection model (208) determines the rectangular coordinates of one or more body parts within the X-ray image (101). The fracture detection module (206) then overlaps the segmentation mask (404) with the body part coordinates, resulting in bounding boxes for each fractured body part.

14 Claims, 5 Drawing Sheets

(51) Int. Cl.
*G06V 10/764* (2022.01)
*G06V 40/10* (2022.01)
*G16H 15/00* (2018.01)

(52) U.S. Cl.
CPC ....... *G16H 15/00* (2018.01); *G06V 2201/033* (2022.01)

(56) References Cited

U.S. PATENT DOCUMENTS

| | | |
|---|---|---|
| 11,315,242 B2 | 4/2022 | Katouzian et al. |
| 2020/0327660 A1* | 10/2020 | Katouzian ................. G06T 7/11 |
| 2021/0233141 A1* | 7/2021 | Ghamsari ............. G06F 16/958 |
| 2022/0230310 A1* | 7/2022 | Xie ........................... G06T 7/62 |
| 2023/0206441 A1* | 6/2023 | Zhong .................... G06V 20/49 |
| 2024/0161479 A1* | 5/2024 | Tyan ...................... G06V 10/42 |

* cited by examiner

SYSTEM AND METHOD FOR PROVIDING BOUNDING BOX TO FRACTURED BODY PARTS IN MUSCULOSKELETAL X-RAY

CROSS REFERENCE TO RELATED APPLICATIONS

The present application claims the benefit of Indian Patent Application No. 202321075164 filed on Nov. 3, 2023, the contents of which are incorporated herein by reference in their entirety.

TECHNICAL FIELD

The present disclosure relates to the field of medical imaging, with a focus on radiological examinations of the musculoskeletal system. More specifically, the present disclosure relates to a system and a method for providing bounding boxes to fractured body parts on the musculoskeletal X-ray image, using an artificial intelligence technique.

BACKGROUND

This section is intended to introduce the reader to various aspects of art, which may be related to various aspects of the present disclosure that are described or claimed below. This discussion is believed to be helpful in providing the reader with background information to facilitate a better understanding of the various aspects of the present disclosure. Accordingly, it should be understood that these statements in this background section are to be read in this light, and not as admissions of prior art. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Fractures are common injuries in patients of all age groups, often resulting from accidents, sports activities, falls and underlying medical conditions like osteoporosis. Timely and accurate fracture detection in patients is crucial for appropriate treatment and management. Traditionally, medical imaging techniques, such as computed tomography (CT) and X-ray imaging, have been the cornerstone for identifying fractures. Conventional X-ray radiography is still a valuable tool in fracture detection. Further, computed tomography (CT) and magnetic resonance imaging (MRI) techniques have improved the accuracy of fracture detection. Such diagnostic techniques are known to necessarily require highly skilled medical professionals, radiologists. Further, conventional instruments used for the diagnostic techniques require appropriate set up, assembling, and operational skills to be worked upon. The medical imaging techniques assist in diagnosis as well as treatment of medical conditions. It is well known that obtaining an X-ray requires at least skilled medical professionals, a lab facility, or a diagnostic center. Further, an interpretation of the X-ray report requires skilled professionals such as radiologists and doctors as well. Typically, non-clinicians such as nurses, physiotherapists, health care providers and patients are not trained and equipped to perform the conventional diagnostic techniques. It may be understood that consulting a doctor, seeking an appointment for conventional X-ray, undergoing the X-ray procedure, procuring the X-ray reports, and then getting the X-ray reports interpreted by doctors, radiologists and the like may become a time-consuming process. Further, there is a possibility of partial diagnosis or an incomplete diagnosis if the X-ray image is not interpreted accurately. Therefore, these methods are complex and time-consuming making them less suitable for rapid diagnosis and point-of-care applications. Artificial intelligence (AI) has revolutionized the healthcare industry by enabling the analysis of patient data, whether in the form of text or medical images. While AI has made significant strides in image recognition, the precise identification of fractures, especially in complex anatomical structures or when subtle fractures are involved, remains a challenge. Conventional systems may fail to highlight the fracture, particularly in complex cases.

The diversity in the presentation of fractures, including variations in size, location, and severity, poses a formidable hurdle. The existing AI models often struggle to generalize effectively across this spectrum, leading to false positives or negatives, and further leading to misdiagnosis or missed fractures. Hence, interpreting complex X-ray images accurately and providing an exact location of fracture, especially in cases with subtle or unconventional fracture patterns, remains a challenge.

Additionally, the robustness of these systems to handle variations in X-ray image quality, positioning, and localization is a concern. Real-world X-ray images can exhibit substantial variability. Therefore, there is a need for an improved system which performs consistently and accurately under such conditions.

Therefore, there exists a long-standing need of a system and a method for providing bounding boxes to fractured body parts on musculoskeletal X-ray images to overcome the above-mentioned problems.

SUMMARY

Before the present system and method and its components are described, it is to be understood that this disclosure is not limited to the system and its arrangement as described, as there can be multiple possible embodiments which are not expressly illustrated in the present disclosure. The present disclosure overcomes one or more shortcomings of the prior art and provides additional advantages discussed throughout the present disclosure. Additional features and advantages are realized through the techniques of the present disclosure.

This summary is not intended to identify essential features of the claimed subject matter nor is it intended for use in detecting or limiting the scope of the claimed subject matter.

In one implementation, a system for providing one or more bounding boxes to fractured body parts detected in musculoskeletal X-ray image is disclosed. In one embodiment, the system may comprise a memory and a processor. Further, the processor may be coupled with the memory. The processor may be configured to execute programmed instructions stored in the memory. Further, the system may comprise a data collection module, a fracture detection module. The data collection module may be configured to collect data which may correspond to an input X-ray image. Furthermore, the system may comprise a fracture detection module. The fracture-detection module may be configured for providing one or more bounding boxes to one or more fractured body parts based on the collected data using a segmentation model and an object detection model based on an artificial intelligence. Furthermore, the segmentation model and the object detection model may be carried out by the processor. The segmentation model may be configured to perform a step of processing the input x-ray image to determine a segmentation score for each pixel of a plurality of pixels of the input x-ray image. Further, the segmentation model may be configured for comparing the segmentation score of each pixel with the segmentation threshold of a fracture to generate a segmentation mask. Further, the object detection model may be configured to perform a step of processing the input x-ray image to determine the rectangular coordinates value of the one or more body parts in the x-ray image. Furthermore, the system may comprise an overlapping module. The overlapping module may be further configured for performing overlapping of the generated segmentation mask and the rectangular coordinates value of the one or more body parts to provide the bounding box to each of the one or more fractured body parts.

In one embodiment, the segmentation score corresponds to score of each pixel corresponding to level of probability of one or more fracture.

In one embodiment, the system may comprise a report generation module to generate a fracture detection report. The fracture detection report may comprise an output X-ray image including the bounding box to each of the one or more fractured body parts.

In another embodiment, the fracture detection module may be trained using data collected by the data collection module.

In one embodiment, the segmentation model may comprise a deep learning algorithm. The deep learning algorithm is one of an EfficientNet, a U-Net, and a combination thereof, based neural network.

In yet another embodiment, the object detection model may comprise a deep learning algorithm. The deep learning algorithm may comprise "you only look once" (YOLO) based neural model to identify and locate one or more body parts, within the input X-ray image.

In yet another embodiment, the object detection model may be trained to determine bounding boxes and class probabilities for one or more body parts present in the input X-ray image.

In another implementation, a method for providing one or more bounding boxes to fractured body parts in musculoskeletal X-ray images is disclosed. The method may comprise a step for collecting data corresponding to an input X-ray image using a data collection module. The method may comprise a step for providing the bounding box to each of one or more body parts based on collected data, using a fracture detection module. The fracture detection module may comprise a segmentation model and an object detection model based on artificial intelligence. The method may comprise a step for processing the input X-ray image to determine a segmentation score for each pixel within the input X-ray image, using the segmentation model. The method may comprise a step for comparing the segmentation scores of each pixel with a segmentation threshold of a fracture to generate a segmentation mask, using the segmentation model. The method may comprise a step for processing the input X-ray image to determine the rectangular coordinates value of one or more body parts within the input X-ray image. The method may comprise a step for performing overlapping of the generated segmentation mask and the rectangular coordinates of the one or more body parts, using an overlapping module, to provide the bounding box to each of the one or more fractured body parts.

In one embodiment, the method may comprise a step for generating a fracture detection report using a report generation module. The fracture detection report may comprise an output X-ray image including a bounding box for each of the one or more fractured body parts.

In yet another embodiment, the method may comprise a step for training the fracture detection module using data collected by the data collection module.

In yet another embodiment, the segmentation model may comprise a deep learning algorithm. The deep learning algorithm may be one of an EfficientNet, a U-Net, and a combination thereof, based neural network.

In yet another embodiment, the object detection model may comprise a deep learning algorithm. The deep learning algorithm may comprise a you only look once (YOLO) based neural model to identify and locate one or more body parts, within the input X-ray image.

In yet another embodiment, the method may comprise a step of training the object detection model to determine bounding boxes and class probabilities for one or more body parts present in the input X-ray image.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The detailed description is described with reference to the accompanying figures. In the Figures, the left-most digit(s) of a reference number identifies the Figure in which the reference number first appears. The same numbers are used throughout the drawings to refer like features and components.

DETAILED DESCRIPTION

Figure 1:
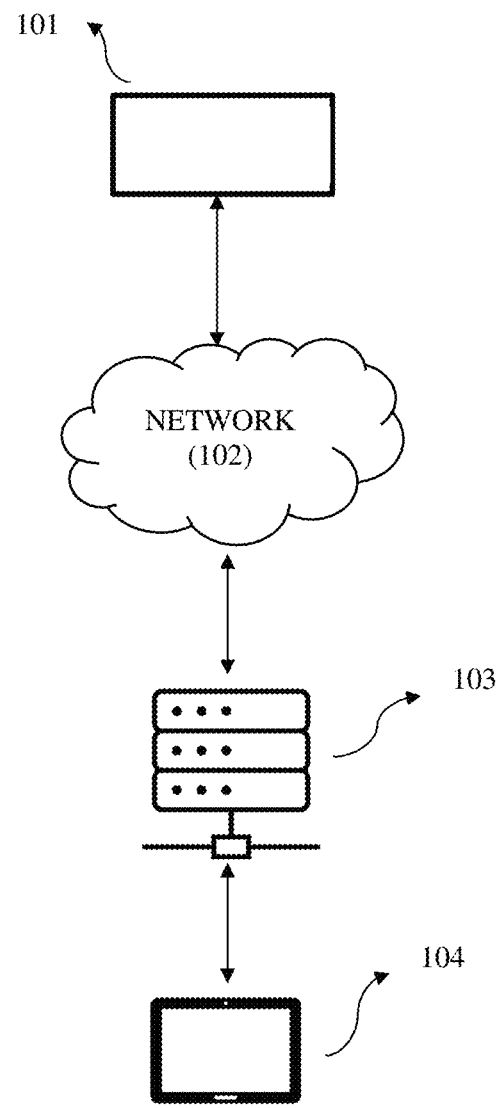
FIG. 1 illustrates a network implementation of a system (100) for providing one or more bounding boxes to fractured body parts in musculoskeletal X-ray, in accordance with an embodiment of the present disclosure.

The terms "comprise", "comprising", "include(s)", or any other variations thereof, are intended to cover a non-exclusive inclusion, such that a setup, system or method that comprises a list of components or steps does not include only those components or steps but may include other components or steps not expressly listed or inherent to such setup or system or method. In other words, one or more elements in a system or apparatus preceded by "comprises . . . a" does not, without more constraints, preclude the existence of other elements or additional elements in the system or apparatus.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures, or characteristics may be combined in any suitable manner in one or more embodiments.

The integration of artificial intelligence (AI) techniques in medical healthcare has revolutionized the industry by leveraging advanced algorithms and machine learning to analyze vast datasets, enhance diagnostic accuracy, personalize treatment plans, and streamline administrative processes.

Conventional systems used in medical healthcare for detecting fractured body parts in X-ray images, face significant limitations. These systems typically rely on rule-based algorithms and manual interpretation, which can lead to inaccuracies and inconsistency in fracture diagnosis. Further, these systems struggle to adapt to variations in image quality, patient anatomy, and fracture subtleties, often missing subtle or complex fractured body parts. Additionally, conventional systems lack the ability to learn and evolve over time, making them less effective in keeping up with advancements in medical knowledge and imaging technology. As a result, there is a pressing need to transition towards more advanced artificial intelligence-based solutions, such as deep learning models, to overcome these challenges and enhance the accuracy and efficiency of fracture detection in medical radiology.

In the light of the above-mentioned limitations, the present subject matter harnesses the artificial intelligence (AI) based, specifically a segmentation model and an object detection model, to provide more accurate and consistent results. The disclosed system may improve the accuracy of providing bounding box(es) to fractured body parts, including subtle ones. The system may be capable to adapt and self-improve over time which ensures superior performance and a personalized fracture detection report, revolutionizing fracture diagnosis in healthcare.

The present disclosure illustrates use of "Artificial intelligence (AI)" in medical image processing. AI is a theory, method, technology and application system that uses a digital computer, or a machine controlled by a digital computer to simulate, extend and expand human intelligence, perceive the environment, acquire knowledge, and use knowledge to obtain the best results. In other words, artificial intelligence is a comprehensive technology of computer science, which attempts to understand the essence of intelligence and produce a new kind of intelligent machine that can react in a similar way to human intelligence. Artificial intelligence is to study the design principles and implementation methods of various intelligent machines, so that the machines have the functions of perception, reasoning and decision-making. AI technology is a comprehensive discipline, covering a wide range of fields, including both hardware-level technology and software-level technology. Basic artificial intelligence technologies generally include technologies such as sensors, dedicated artificial intelligence chips, cloud computing, distributed storage, big data processing technologies, operation/interaction systems, and mechatronics. Artificial intelligence software technology mainly includes computer vision technology, speech processing technology, natural language processing technology, and machine learning/deep learning.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional). For example, machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging evaluation may be supplemented or substituted by any number of other algorithm-based approaches, including variations of artificial neural networks, learning-capable algorithms, trainable object classifications, and other artificial intelligence processing techniques.

In one non-limiting embodiment, a system for providing bounding boxes corresponding to fractured body parts in musculoskeletal X-ray image is disclosed. The system may include a variety of data collected in the form of X-ray image data. The segmentation model and the object detection model based on an artificial intelligence may correspond to a deep learning-based imaging model, which helps in providing bounding boxes to one or more fractured body parts from musculoskeletal X-ray image in an intelligent manner. The system may be capable of learning from its operation, improving its fracture detection capabilities over time. The system can learn from each interaction, continuously refining its understanding of individual data and corresponding to the bounding boxes to fractured body parts in musculoskeletal X-ray image.

Now referring to FIG. 1, a block diagram describing a system (100) for providing one or more bounding boxes to fractured body parts in musculoskeletal X-ray, is illustrated in accordance with an embodiment of a present subject matter. The system (100) may include a variety of data collected in the form of an input X-ray image (101). The collected data is coupled with a server (103) via a network (102) connection. Further, considering that the system (100) is implemented on a server (103), it may be understood that the system (100) may be accessed via a variety of computing systems (104). The computing system (104) may correspond to an interface which enables the user to interact with the system (100). The computing system (104) may comprise one selected from a group consisting of a cell phone, personal digital assistant (PDA), laptop computer, stationary personal computer, IPTV remote control, web tablet, laptop computer, pocket PC, a television set capable of receiving IP based video services and mobile IP device.

Figure 2:
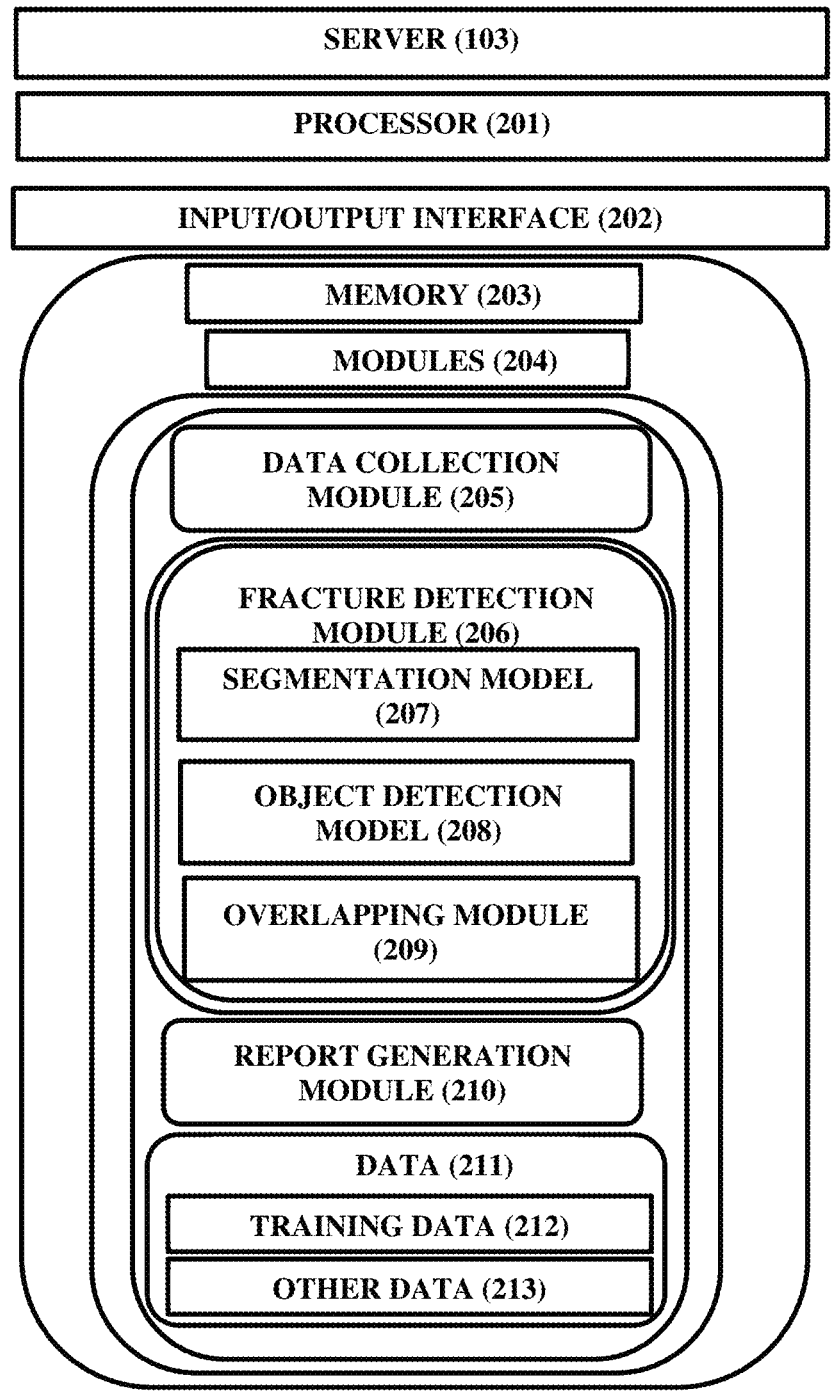
FIG. 2 illustrates a block diagram (200) of a server (103), in accordance with the embodiment of the present disclosure.

In an embodiment, the system (100) may be configured to receive user data from one or more users, via the computing system (104). The collected data may be in the form of the input X-ray image (101) data. In an embodiment, the input X-ray image (101) is collected by the server (103) via the network (102), and is transmitted to a memory (203) (as illustrated in FIG. 2) for storage. Further, the functionality and other characteristics of the server (103) would be provided in description of FIG. 2.

In yet another embodiment, the collected data (101), the server (103) and the computing system (104) may communicate with each other via the network (102). In one implementation, the network (102) may be a wireless network, a wired network, or a combination thereof. The network (102) can be implemented as one of the different types of networks, such as intranet, local area network (LAN), wide area network (WAN), the internet, and the like. The network (102) may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network (102) may include a variety of network devices, including routers, bridges, servers, computing devices, storage devices, and the like.

In another embodiment, the network (102) may include any one of the following: a cable network, the wireless network, a telephone network (e.g., Analog, Digital, POTS, PSTN, ISDN, xDSL), a cellular communication network, a mobile telephone network (e.g., CDMA, GSM, NDAC, TDMA, E-TDMA, NAMPS, WCDMA, CDMA-2000, UMTS, 3G, 4G, 5G, 6G), a radio network, a television network, the Internet, the intranet, the local area network (LAN), the wide area network (WAN), an electronic positioning network, an X.25 network, an optical network (e.g., PON), a satellite network (e.g., VSAT), a packet-switched network, a circuit-switched network, a public network, a private network, and/or other wired or wireless communications network configured to carry data.

The system (100) can be implemented using hardware, software, or a combination of both, which includes using where suitable, one or more computer programs, mobile applications, or "apps" by deploying either on-premises over the corresponding computing terminals or virtually over cloud infrastructure. The system (100) may include various micro-services or groups of independent computer programs which can act independently in collaboration with other micro-services. The system (100) may also interact with a third-party or external computer system. Internally, the system (100) may be the central processor of all requests for transactions by the various actors or users of the system. A critical attribute of the system (100) is that it can concurrently and instantly complete an online transaction by a system user in collaboration with other systems.

Now, referring to FIG. 2, a block diagram (200) showing an overview of the server (103) for providing one or more bounding boxes to fractured body parts on musculoskeletal X-ray image (101), is illustrated in accordance with an embodiment of a present subject matter. The server (103) includes a processor (201), an input/output (I/O) interface (202), and the memory (203). The processor (201) is coupled with the memory (203). The processor (201) is configured to execute programmed instructions stored in the memory (203). The processor, in one embodiment, may comprise a standard microprocessor, microcontroller, central processing unit (CPU), distributed or cloud processing unit, state machines, logic circuitries, and/or any devices that manipulate signals based on operational instructions and/or other processing logic that accommodates the requirements of the present invention.

Further, the I/O interface (202) is an interface to other components of the server (103) and the system (100). The I/O interface (202) may include a variety of software and hardware interfaces, for example, a web interface, a graphical user interface, and the like. The I/O interface (202) may allow the system (100) to interact with the user directly or through the computing devices (104). Further, the I/O interface (202) may enable the system (100) to communicate with other computing devices, such as web servers and external data servers (not shown). The I/O interface (202) can facilitate multiple communications within a wide variety of networks and protocol types, including wired networks, for example, LAN, cable, etc., and wireless networks, such as WLAN, cellular, or satellite. The I/O interface (202) may include one or more ports for connecting a number of devices to one another or to another server. In one embodiment, the I/O interface (202) allows the server (103) to be logically coupled to other computing systems (104), some of which may be built in. Illustrative components include tablets, mobile phones, scanner, printer, wireless device, etc.

Further, the processors (201) can read data from various entities such as memory (203) or I/O interface (202). The processor's (201) primary functions encompass data acquisition, wherein it gather input X-ray image (101). Following this, the collected data undergoes analysis through specialized modules, and the system (100) computes a fracture detected body part. Ultimately, it generates an output, which typically includes a diagnosis or evaluation on the fractured body part, informed by the comprehensive analysis of the X-ray image. In one exemplary embodiment, the body part may include, but not limited to comprising ankle, leg, clavicle, femur, fibula tibia, wrist, forearm, humerus, shoulder, foot, elbow, hand, knee, finger, hip, pelvis, toe, chest.

The memory (203) may include any computer-readable medium or computer program product known in the art including, for example, volatile memory, such as static random-access memory (SRAM) and dynamic random-access memory (DRAM), and/or non-volatile memory, such as read only memory (ROM), erasable programmable ROM, flash memories, hard disks, Solid State Disks (SSD), optical disks, magnetic tapes, memory cards, virtual memory and distributed cloud storage. The memory (203) may be removable, non-removable, or a combination thereof. The memory (203) may include routines, programs, objects, components, data structures, etc., which perform particular tasks or implement particular abstract data types. The memory (203) may include programs or coded instructions that supplement applications and functions of the system (100).

In one embodiment, the memory (203), amongst other things, serves as a repository for storing data processed, received, and generated by one or more of the programs or the coded instructions. In yet another embodiment, the memory (203) may be managed under a federated structure that enables adaptability and responsiveness of the server (104). The memory further may include various modules (204) namely a data collection module (205), a fracture detection module (206), and a report generation module (210). The fracture detection module (206) may further include a segmentation model (207), an object detection model (208) and an overlapping module (209). In one embodiment, the server (103) utilizes the processor (201) for executing the various modules (204) stored in the memory (203).

The data collection module (205) is configured to collect data corresponding to the input X-ray image (101). In an exemplary embodiment, the input X-ray image corresponds to a part of the body. The data collected by the data collection module (205) is utilized by the fracture detection module (206) for detecting the one or more body parts and to provide the one or more bounding boxes to one or more fractured body parts. In one exemplary embodiment, the fracture detection module (206) is implemented by using an artificial intelligence-based system. In one implementation, the fracture detection module (206) analyses the input X-ray image (101) by using the artificial intelligence-based system and generates an output of each fracture provided with the bounding box of one or more fractured body parts detected in the input X-ray image. In an embodiment, the fracture detection module (206) may utilize the processor (201) to implement the artificial intelligence-based system. The artificial intelligence-based system corresponds to a combination of the segmentation model (207) and the object detection model (208).

Figure 4:
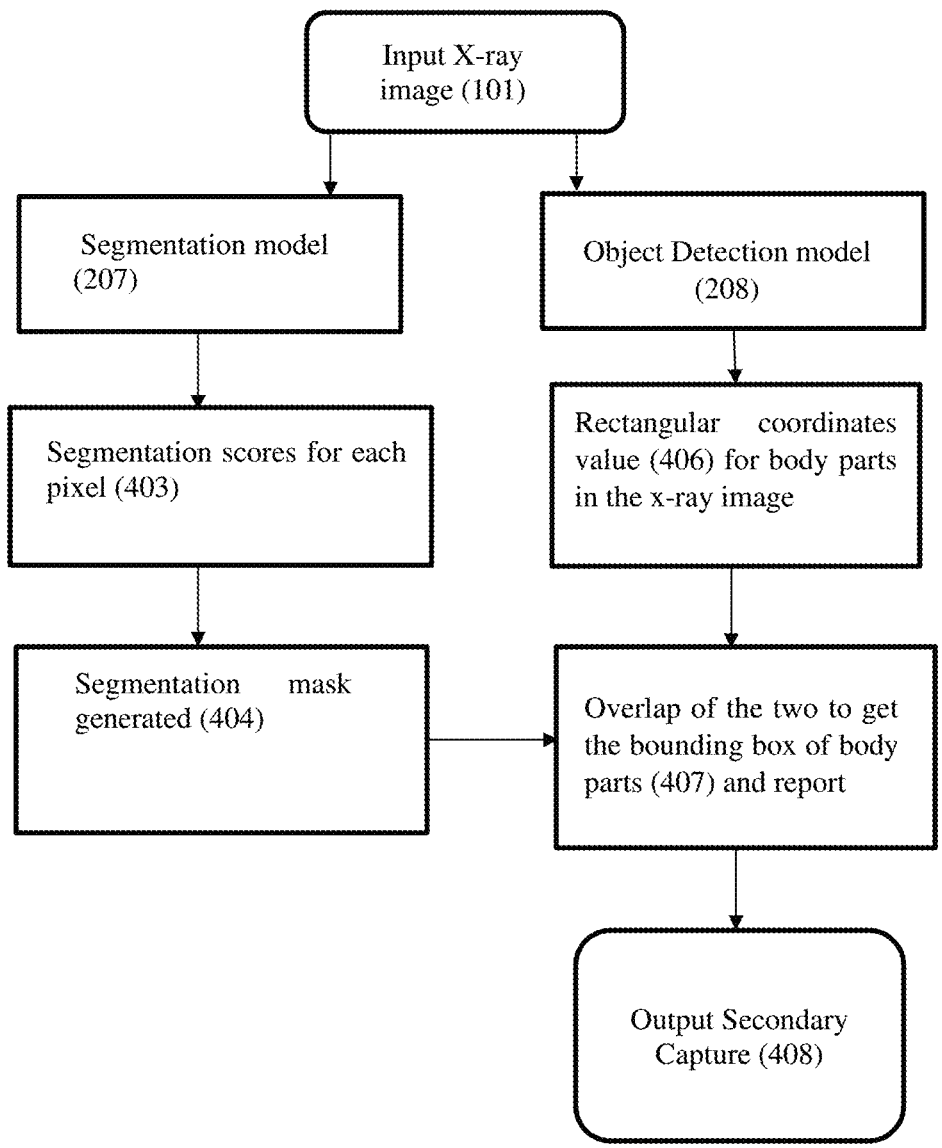
FIG. 4 illustrates a flowchart describing a working (400) of the system (100) for providing one or more bounding boxes to fractured body parts in musculoskeletal X-ray, in accordance with an embodiment of the present disclosure.

Now referring to FIG. 2 and FIG. 4, the fracture detection module (206) may comprise the segmentation model (207) and the object detection model (208). The fracture detection module (206) may train the artificial intelligence-based system, including the segmentation model (207) and the object detection model (208), using the input X-ray image (101). The trained model may correspond to data learned by the system to operate efficiently. The trained model may enable an accurate operation of the deep learning techniques. In one aspect, the historical data may comprise historical clinical reports and historical X-ray images associated with the set of patients. In another aspect, the historical data may comprise previous X-ray images of the patient.

In one embodiment, the segmentation model (207) may corresponds to Unet++ based algorithm for the segmentation task keeping EfficientNetv2 as the backbone. EfficientNetv2 is a family of the convolutional neural network architectures designed for efficient and scalable image classification. It introduces compound scaling to balance model depth, width, and resolution, achieving high accuracy with fewer parameters. UNet++ is the convolutional neural network architecture commonly used for semantic segmentation tasks. It combines an encoder-decoder structure with skip connections to capture global and local features. UNet++ has been widely adopted and achieved state-of-the-art results in various medical imaging and computer vision applications.

Ground truth masks are annotated by a team of expert radiologists over a span of one year to draw free-hand boundaries across fractured body parts on the X-rays and mark the labels as positive. The present system and method collected 550 thousand X-ray scans and used 400 thousand for training and the remaining for validation. The input X-ray may contain multiple fractured body parts consisting of frontal, lateral, and oblique views.

The segmentation model (207) may use Dice-BCE loss the segmentation task. The Dice BCE (Binary Cross-Entropy) loss combines the Dice coefficient loss and the Binary Cross-Entropy loss. The former computes dissimilarity between the predicted and ground truth segmentation masks, encouraging accurate localization and segmentation by maximizing their overlap.

In another embodiment, the segmentation model (207) is trained on three GPUs (NVIDIA GeForce RTX 3090) for 130 epochs with a batch size of 10000, and Stochastic Gradient Descent (SGD) optimizer. The OneCycleLR, a learning rate scheduler is used to optimize the training process by dynamically adjusting the learning rate during different stages of training. It involves gradually increasing and then decreasing the learning rate within a single training cycle. This technique aims to improve convergence speed, prevent overfitting, and achieve better generalization performance.

The segmentation model (207) may be configured to process the input x-ray image to determine a segmentation score for each pixel (403) of a plurality of pixels of the input x-ray image. Further, the segmentation score of each pixel (403) is compared with the segmentation threshold of a fracture to generate a segmentation mask (404). In one embodiment, the segmentation mask may comprise a fracture mask. In one exemplary embodiment, the segmentation score corresponds to score of each pixel corresponding to level of probability of fracture.

In one embodiment, the object detection model (208) may correspond to a deep learning algorithm. In one exemplary embodiment, the deep learning algorithm may comprise a you only look once (YOLO) based neural model to identify and locate one or more body parts, within the input X-ray image (101). The object detection model (208) may be trained to determine bounding boxes and class probabilities for one or more body parts present in the input X-ray image (101).

In another embodiment, the object detection model (208) may be configured to process the input X-ray image (101) to determine the rectangular coordinates of one or more body parts in the input X-ray image (101).

Further, the fracture detection module (206) may comprise the overlapping module (209) for performing overlapping of the generated segmentation mask (404) and the rectangular coordinates value of the one or more body parts to provide the bounding box to each of the one or more fractured body parts.

The overlapping module (209) may be essential for overlapping the boundaries of one or more body parts determined by rectangular coordinates value with one or more fractures obtained by the segmentation mask from the input X-ray image, potentially resulting in generation of individual bounding box for each fractured body parts.

Figure 3:
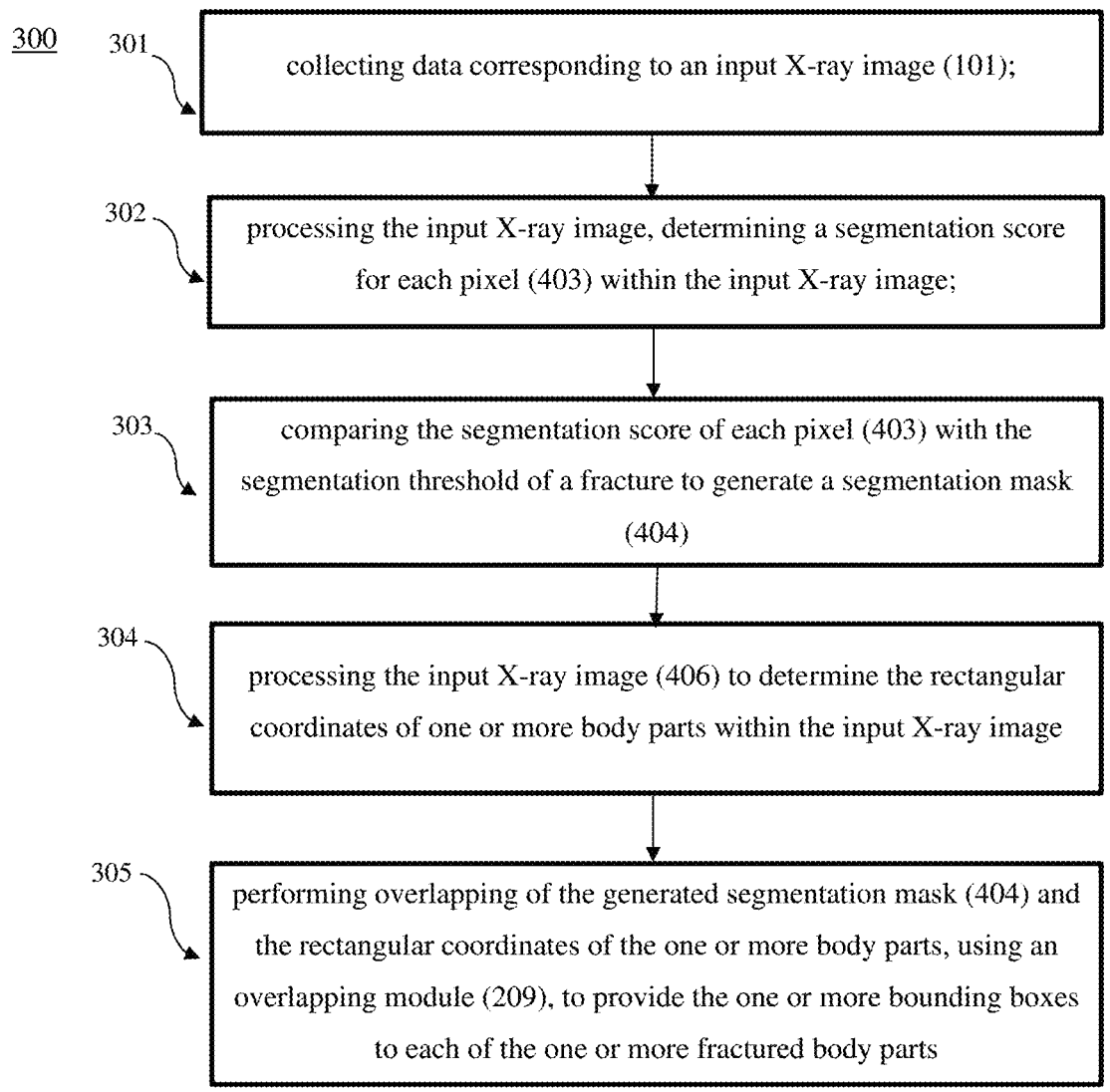
FIG. 3 illustrates a flowchart describing a method (300) for providing one or more bounding boxes to fractured body parts in musculoskeletal X-ray, in accordance with an embodiment of the present disclosure.

Referring to FIG. 3 a method (300) for providing one or more bounding boxes to fractured body parts in musculoskeletal X-ray is disclosed.

At step (301), the method (300) may comprise collecting data corresponding to the input X-ray image using a data collection module (205).

At step (302), the method (300) may comprise processing the input x-ray image to determine a segmentation score for each pixel (403) of a plurality of pixels of the input x-ray image (101), using a segmentation model (207).

At step (303), the method (300) may comprise comparing the segmentation score of each pixel (403) with the segmentation threshold of a fracture, using the segmentation model (207), to generate a segmentation mask (404).

At step (304), the method (300) may comprise processing the input x-ray image (101) to determine the rectangular coordinates value of the one or more body parts in the input x-ray image (101).

At step (305), the method (300) may comprise performs overlapping of the generated segmentation mask (404) and the rectangular coordinates value (406) of the one or more body parts to provide the bounding box to each of the one or more fractured body parts.

The method (300) may further comprise a step for generating the output secondary capture (408).

Figure 5:
FIG. 5 illustrates a report (500) generated by the report generation module (210), in accordance with an embodiment of the present subject matter.

Now referring to FIG. 5, a diagram showing a report (500) generated by the report generation module (210), is illustrated in accordance with an embodiment of a present subject matter. The report generation module (210) may generate the fracture detection report (500) with an output X-ray image including a bounding box to each of the one or more fractured body parts and presents name of fractured body part. In one exemplary embodiment, the fractured body is humerus.

Example

Normal scenario (unaided): The process often begins with the patient reporting when a patient presents with symptoms suggestive of a musculoskeletal injury, the diagnostic process follows a systematic protocol. The healthcare provider may begin by gathering a detailed medical history, where the healthcare provider inquiries about the circumstances of the injury, the patient's description of pain or discomfort, and any related symptoms. Subsequently, a thorough physical examination of the affected area is conducted to assess for visible signs such as swelling, tenderness, deformities, or bruising. The patient's range of motion and any pain associated with movement are also evaluated. Recognizing the limitations of manual examinations, healthcare providers often resort to diagnostic imaging techniques like X-rays to visualize internal structures and identify potential body parts. In such cases, the patient is referred to the radiology department, where trained technologists capture X-ray images of the injured area. Once obtained, these images are then scrutinized by a radiologist who examines them for any telltale signs of a fracture, such as breaks, misalignment, or other anomalies within the bones. The healthcare provider integrates the information obtained from the physical examination and the interpretation of the X-ray images to formulate a diagnosis. This traditional approach, while generally effective, relies heavily on the experience and judgment of healthcare professionals. It can occasionally result in delays in diagnosis and treatment planning, underscoring the need for more advanced and efficient diagnostic tools in the field of musculoskeletal injuries.

Using Disclosed System (Aided): The system and method disclosed in the present invention could be used to assist by providing one or more bounding boxes to fractured body parts on musculoskeletal x-ray image and enhances the diagnostic process. The healthcare professionals would input the X-ray image of the affected body part, and any other relevant clinical data into the device. The AI model would analyze the X-ray image to detect any abnormalities, such as fractured detected, fracture types, fractured body parts. The system inputs the X-ray image and employs the segmentation model to determine the segmentation score for each pixel within the image, and subsequently compares each pixel's segmentation score with the segmentation threshold of a fracture to generate the segmentation mask. Simultaneously, the object detection model processes the X-ray image to determine the rectangular coordinates value of one or more body parts and performs an overlapping operation between the generated segmentation mask and the rectangular coordinates. The process yields the bounding box for each fracture, offering valuable diagnostic support to healthcare professionals. With these results, healthcare professionals can make more informed diagnoses and recommend suitable treatment options.

The system (100) as disclosed in the disclosure may provide valuable support in clinical decision-making, offering several advantages for the detection of affected body part, including the following:

Enhanced Accuracy: Utilizes artificial intelligence to improve fracture detection accuracy, reducing the likelihood of misdiagnosis.

Subtle Fracture Detection: Capable of identifying subtle or hairline fractures that might be missed by human observers.

Efficiency: Automates the detection process, saving time for medical professionals.

Personalized Reports: Generates fracture detection reports, aiding in treatment decisions.

Adaptability: Can be trained and improved with more data, adapting to evolving medical knowledge and image variations.

Advanced Technology: Utilizes deep learning models, including convolutional neural networks (CNNs) and U-Net based networks, YOLO based neural networks, for detecting body parts and providing bounding box to each fracture.

Various modifications to the embodiment will be readily apparent to those skilled in the art and the generic principles herein may be applied to other embodiments. However, one of ordinary skill in the art will readily recognize that the present disclosure is not intended to be limited to the embodiments illustrated but is to be accorded the widest scope consistent with the principles and features described herein.

The foregoing description shall be interpreted as illustrative and not in any limiting sense. A person of ordinary skill in the art would understand that certain modifications could come within the scope of this disclosure.

The embodiments, examples and alternatives of the preceding paragraphs or the description and drawings, including any of their various aspects or respective individual features, may be taken independently or in any combination. Features described in connection with one embodiment are applicable to all embodiments unless such features are incompatible.

The invention claimed is:

1. A system (100) for providing one or more bounding boxes (501) to one or more fractured body parts in musculoskeletal X-ray image, characterized in that, the system (100) comprises:
a memory (203);
a processor (201) coupled with the memory (203), wherein the processor (201) is configured to execute programmed instructions stored in the memory (203);
a data collection module (205), wherein a data collected by the data collection module (205) corresponds to an input x-ray image (101);

a fracture detection module (206) for providing the one or more bounding boxes (501) to the one or more fractured body parts based on the collected data, using a segmentation model (207) and an object detection model (208) based on an artificial intelligence, wherein the segmentation model (207) and the object detection model (208) carried out by the processor (201),
  wherein the segmentation model (207) is configured to perform steps of:
    processing the input x-ray image (101) to determine a segmentation score for each pixel (403) of a plurality of pixels of the input x-ray image (101);
    comparing the segmentation score of each pixel (403) with a segmentation threshold of a fracture to generate a segmentation mask (404);
  wherein the object detection model (208) is configured to perform steps of:
    processing the input x-ray image (101) to determine a rectangular coordinates value (406) of one or more body parts in the input x-ray image (101);
  performing by an overlapping module (209), overlapping of the generated segmentation mask (404) and the rectangular coordinates value (406) of the one or more body parts to provide the one or more bounding boxes (501) to each of the one or more fractured body parts.

2. The system (100) as claimed in claim 1, wherein the segmentation score corresponds to score of each pixel corresponding to level of probability of fracture.

3. The system (100) as claimed in claim 1, wherein the system (100) comprises a report generation module (210) to generate a fracture detection report (500), wherein the fracture detection report (500) comprises an output X-ray image including the one or more bounding boxes (501) to each of the one or more fractured body parts.

4. The system (100) as claimed in claim 1, wherein the fracture detection module (206) is trained using the data collected by the data collection module (205).

5. The system (100) as claimed in claim 1, wherein the segmentation model (207) comprises a deep learning algorithm, wherein the deep learning algorithm is one of an EfficientNet, a U-Net, and a combination thereof, based neural network.

6. The system (100) as claimed in claim 1, wherein the object detection model (208) comprises a deep learning algorithm, wherein the deep learning algorithm comprises a you only look once (YOLO) based neural model to identify and locate the one or more body parts, within the input X-ray image (101).

7. The system (100) as claimed in claim 6, wherein the object detection model (208) is trained to determine the one or more bounding boxes and class probabilities for the one or more body parts present in the input X-ray image (101).

8. A method (300) for providing one or more bounding boxes (501) to one or more fractured body parts in musculoskeletal X-ray image, the method comprising the steps of:
  collecting (301) data corresponding to an input X-ray image (101) using a data collection module (205);
  providing the one or more bounding boxes (501) to each of the one or more fractured body parts based on the collected data, using a fracture detection module (206), wherein the fracture detection module (206) comprises a segmentation model (207) and an object detection model (208) based on an artificial intelligence,
    wherein the segmentation model (207) performs the following steps:
      processing (302) the input X-ray image (101) to determine a segmentation score for each pixel (403) within the input X-ray image (101);
      comparing (303) the segmentation score of each pixel (403) with a segmentation threshold of a fracture to generate a segmentation mask (404);
    wherein the object detection model (208) performs the following steps of:
      processing (304) the input X-ray image (101) to determine a rectangular coordinates value (406) of one or more body parts within the input X-ray image (101);
  performing (305), overlapping of the generated segmentation mask (404) and the rectangular coordinates value (406) of the one or more body parts, using an overlapping module (209), to provide the one or more bounding boxes (501) to each of the one or more fractured body parts.

9. The method (300) according to claim 8, wherein the segmentation score corresponds to score of each pixel corresponding to level of probability of fracture.

10. The method (300) according to claim 8, further comprises a step for generating a fracture detection report (500) using a report generation module (210), wherein the fracture detection report (500) comprises an output X-ray image including the one or more bounding boxes (501) for each of the one or more fractured body parts.

11. The method (300) according to claim 8, comprises a step for training of the fracture detection module (206) using the data collected by the data collection module (205).

12. The method (300) as claimed in claim 8, wherein the segmentation model (207) comprises a deep learning algorithm, wherein the deep learning algorithm is one of an EfficientNet, a U-Net, and a combination thereof, based neural network.

13. The method (300) as claimed in claim 8, wherein the object detection model (208) comprises a deep learning algorithm, wherein the deep learning algorithm comprises a you only look once (YOLO) based neural model to identify and locate the one or more body parts, within the input X-ray image (101).

14. The method (300) as claimed in claim 13, comprises a step for training the object detection model (208) to determine the one or more bounding boxes and class probabilities for one or more body parts present in the input X-ray image (101).

* * * * *